United States Patent
Hoek et al.

(10) Patent No.: US 6,517,481 B2
(45) Date of Patent: Feb. 11, 2003

(54) METHOD AND SENSOR FOR WIRELESS MEASUREMENT OF PHYSIOLOGICAL VARIABLES

(75) Inventors: Bertil Hoek, Vaesteras (SE); Ola Hammarstroem, Vaestra Goetaland (SE); Per Benkowski, Uppsala (SE); Paer von Malmborg, Uppsala (SE); Lars Tenerz, Uppsala (SE)

(73) Assignee: Radi Medical Systems AB, Uppsala (SE)

( * ) Notice: Subject to any disclaimer, the term of this patent is extended or adjusted under 35 U.S.C. 154(b) by 0 days.

(21) Appl. No.: 09/949,951

(22) Filed: Sep. 12, 2001

(65) Prior Publication Data

US 2002/0013527 A1 Jan. 31, 2002

Related U.S. Application Data

(62) Division of application No. 09/219,798, filed on Dec. 23, 1998.

(51) Int. Cl.[7] ............................. A61B 5/00; A61B 8/00
(52) U.S. Cl. ....................................... 600/300; 600/438
(58) Field of Search .................. 600/407, 409, 600/437–438, 585, 462–471, 561, 573; 73/636; 367/2

(56) References Cited

U.S. PATENT DOCUMENTS

| | | | | |
|---|---|---|---|---|
| 3,853,117 A | | 12/1974 | Murr .......................... 128/2 V |
| 3,893,111 A | | 7/1975 | Cotter ..................... 343/6.5 R |
| 4,026,276 A | | 5/1977 | Chubbuck ................... 128/2 P |
| 4,109,644 A | | 8/1978 | Kojima ......................... 600/437 |
| 4,127,114 A | | 11/1978 | Bretscher ..................... 600/480 |
| 4,513,750 A | * | 4/1985 | Heyman et al. .............. 600/438 |
| 4,920,967 A | * | 5/1990 | Cottonaro .................... 600/465 |
| 5,005,577 A | | 4/1991 | Frenkel ....................... 128/645 |
| 5,329,927 A | * | 7/1994 | Gardineer et al. ........... 600/461 |
| 5,581,144 A | * | 12/1996 | Corl et al. ................... 310/369 |
| 5,619,997 A | | 4/1997 | Kaplan ................... 128/660.02 |
| RE35,648 E | | 11/1997 | Tenerz et al. ................ 128/673 |
| 5,704,352 A | | 1/1998 | Tremblay et al. ........... 600/300 |
| 5,747,705 A | | 5/1998 | Herb et al. ............... 73/862.59 |
| 5,792,055 A | * | 8/1998 | McKinnon ................... 600/140 |
| 5,808,210 A | | 9/1998 | Herb et al. ............... 73/862.59 |
| 5,989,190 A | | 11/1999 | Kaplan ......................... 600/438 |
| 6,224,554 B1 | * | 5/2001 | Tickner et al. .............. 600/438 |
| 6,261,247 B1 | * | 7/2001 | Ishikawa et al. ............ 600/410 |
| 2001/0037066 A1 | * | 11/2001 | Smith .......................... 600/462 |

FOREIGN PATENT DOCUMENTS

| | | |
|---|---|---|
| EP | 0 420 177 | 4/1991 |
| WO | 98/43701 | 10/1998 |

OTHER PUBLICATIONS

Backlund, Y., et al., "Passive Silicon Transensor Intended for Biomedical, Remote Pressure Monitoring," Sensors and Actuators, A21–A23, pp. 58–61 (1990).

Rosengren, L., et al., "A System for Wireless Intro–Ocular Pressure Measurements Using a Silicon Micromachined Sensor," J. of Micromech. Microeng., vol. 2, pp. 202–204 (1992).

Rosengren, L., et al., A System for Passive Implantable Pressure Sensors, Sensors and Actuators, A, pp. 1–4 (1994).

* cited by examiner

Primary Examiner—Francis J. Jaworski
(74) Attorney, Agent, or Firm—Foley & Lardner

(57) ABSTRACT

The sensor and guide wire assembly having a sensor element is inserted into the patient's body. Acoustic or electromagnetic waves are them emitted from an external source toward the sensor element. The sensor element receives the incident waves and enters into a resonating state. The characteristics of the resonance correspond to the variable or variables to be measured. A transducer is located externally from the patient's body and receives the scattered wave and transmits a resultant signal to an electronic drive and detection unit for signal analysis.

6 Claims, 8 Drawing Sheets

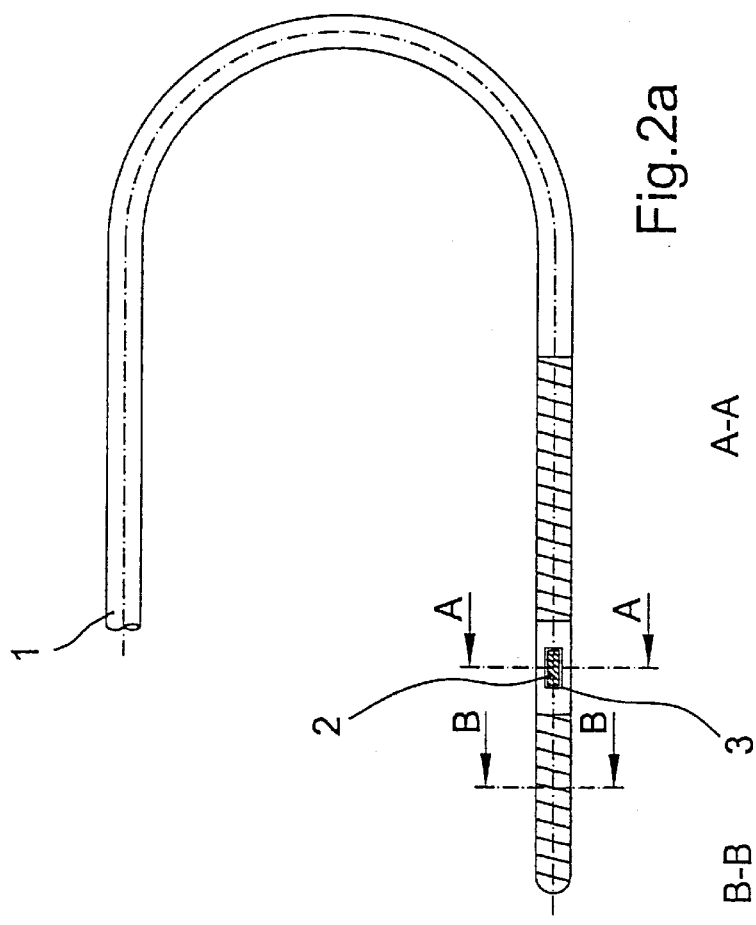
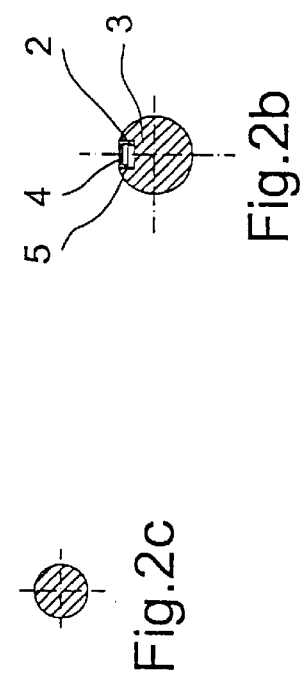
Fig.2a
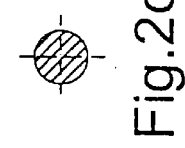
Fig.2b
Fig.2c

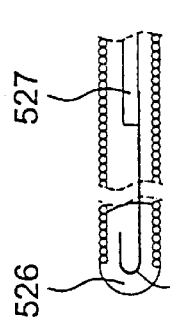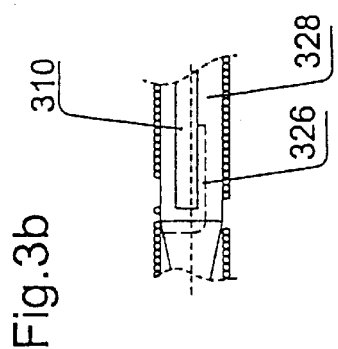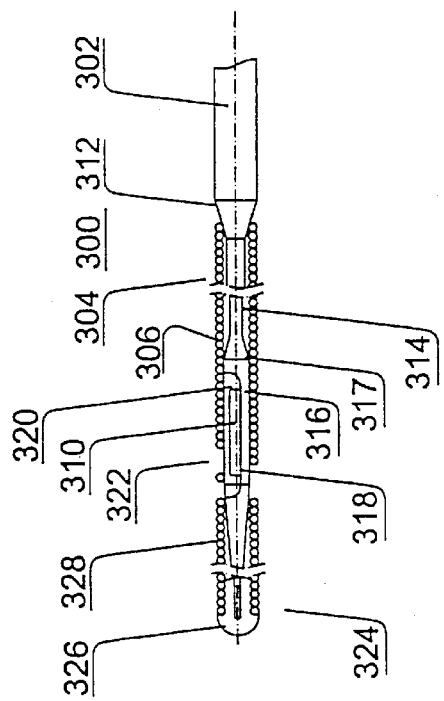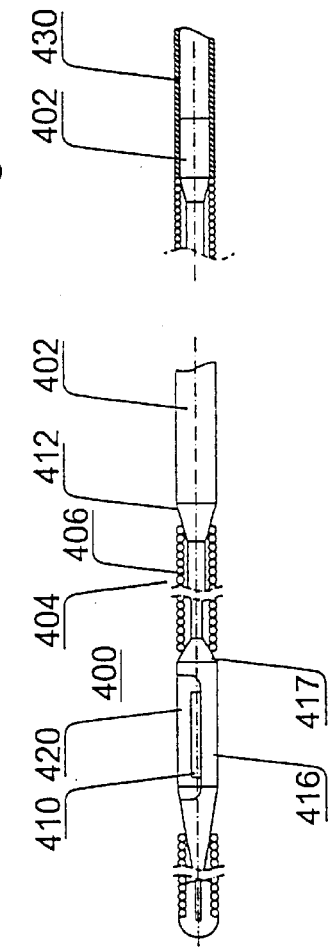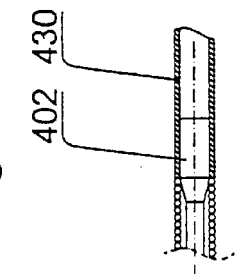

METHOD AND SENSOR FOR WIRELESS MEASUREMENT OF PHYSIOLOGICAL VARIABLES

This is a Divisional application of application No. 09/219,798, filed Dec. 23, 1998.

BACKGROUND OF THE INVENTION

1. Field of the Invention

The invention relates to a novel method, system, sensor and sensor/guide wire assembly for measuring physiological variables inside the body of a human or an animal. More particularly, it relates to a wireless sensor having a diaphragm comprising elements responsive to resonance.

2. Description of Related Art

Intravascular measurements of pressure, flow, and temperature via sensors mounted to guidewires, as disclosed in U.S. Pat. No. 5,226,423, Tenerz, reissued as Re. 35,648, are of particular interest to the health care industry, and serve as tangible examples of embodiments of system solutions, device designs, components and materials to be used in the realization of the invention.

Implantable devices for physiological measurements and therapy have been used for decades, for example, in combination with cardiac pacemakers. These device carry their own power supply, are relatively bulky, and require a surgical procedure to be implanted into the patient's body.

For short term diagnostic procedures, such as intravascular measurements of pressure, flow, and temperature, the current state of the art utilizes micromechanical sensor elements, mostly silicon devices based on well known piezoresistive, capacitive, or fiber optic principles. The devices communicate information and power along a guidewire via thin optical fibers or insulated electrical leads. The guidewire is extremely small, preferably with an overall diameter no larger than 0.4 mm. Housing multiple wires in a guide wire with such an extremely small area is very difficult from a technological standpoint and is also very costly. Other difficulties arise, including, maintaining the structural integrity and the mechanical properties of the guidewire while encompassing within the guide wire the power and information transmission media. Moreover, weak points, in terms of sensor performance (e.g., zero point stability) and mechanical reliability, exist at the connecting points between the sensor and the information and power transmission wires.

A wireless system for recording pressure in the eye is disclosed in the following articles: "Passive Silicon Transensor Intended for Biomedical, Remote pressure Monitoring" by Bäcklund, Y. et al in *Sensors and Actuators*, A21–A23 (1990) 58–61, Elsevier Sequoia; "A System for Wireless Intra-ocular Pressure Measurements Using Silicon Micromachined sensor" by Rosengren, L. et al. in *J. Of Micromech. Microeng.* 2(1992) 202–204, IOP Publishing Ltd; and "A system for Passive Pressure Implantable Pressure Sensors" by Rosengren, L. et al in *Sensors and Actuators* A, 1994, Elsevier Sequoia. The disclosures of these publications are hereby incorporated in this specification by reference.

The wireless system disclosed in these articles comprises an electromagnetic sensor device of an L-C circuit type, having the capability of resonating in response to an excitation by an externally applied electromagnetic field, and to change is resonance frequency in response to a pressure change. The sensor is implanted/inserted into the eye, and excitation energy is applied. The shift in resonance frequency due to change in pressure exerted on the device is registered.

The difficulties suggested in the preceding are not intended to be exhaustive but rather are among many which tend to reduce the desirability of the known devices. Other noteworthy problems may exist; however, those presented above should be sufficient to demonstrate that such methods and apparatuses appearing in the past will admit to worthwhile improvement.

SUMMARY OF THE INVENTION

Accordingly, it is therefore a general object of the invention to provide a method and apparatus that will obviate or minimize difficulties of the type previously described.

It is a specific object of the invention to provide a method and device for measuring physiological variables able to transmit information without the use of wires.

It is another object of the invention to provide a device with high mechanical reliability for measuring physiological variables.

It is still another object to provide a relatively small device for measuring physiological variables.

It is a further object to provide a device for measuring physiological variables that has virtually no weak points.

It is yet a further object of the invention to provide a device that can be produced in a cost effective manner.

It is still a further object of the invention to provide a method for measuring physiological variables inside a human or an animal body.

For the purpose of this application, a "resonance sensor" is meant to encompass any device that has the capability of resonating at a defined frequency upon excitation by energy/power from an external source, i.e. without physical contact between source and device, and in addition to have the capability of changing its resonance frequency in a defined way as a result of a change of a physical variable, such as pressure, temperature or fluid flow, that the device is being exposed to. Alternatively, the quality factor of the resonating device may be affected by said change, and can be used for detection purposes.

A preferred embodiment of the invention that is intended to accomplish at least some of the foregoing objects includes a guidewire and a sensor element attached to said guidewire, wherein said sensor element has no wires for transmitting or receiving information. A preferred method includes inserting a guidewire into a patient's body; transmitting waves to a sensor mounted on the guidewire; redistributing the waves, the redistributing being a function of the physiological variable; and receiving the redistributed waves.

Additional objects and advantages of the invention will be set forth in the description that follows, and in part will be obvious from the description, or may be learned by practice of the invention. The objects and advantages of the invention may be realized and obtained by means of the instruments and combinations particularly pointed out in the appended claims.

BRIEF DESCRIPTION OF THE DRAWINGS

The accompanying drawings, which are incorporated in and constitute a part of the specification, illustrate a number of presently preferred embodiments of the invention, and, together with the general description of the preferred embodiment below, serve to explain the principles of the invention.

FIG. 2a is a schematic view of a sensor and guide wire assembly in general;

FIG. 2b is a crossection at A—A in FIG. 2a;

FIG. 2c is a crossection at B—B in FIG. 2a

FIG. 3a is a longitudinal view of a embodiment of a sensor and guide wire assembly according to the invention;

FIG. 3b is a detail view of a sensor mounting site;

FIG. 4a is a longitudinal view of another embodiment of a sensor and guide wire assembly according to the invention;

FIG. 4b is a detail view of a part of a sensor and guide wire assembly according to the invention;

FIG. 5b is a cross section of the very distal part of a sensor and guide wire assembly according to the invention;

FIG. 10b shows a vibration mode of the embodiment of FIG. 10a;

DETAILED DESCRIPTION OF THE PREFERRED EMBODIMENTS

Figure 1:
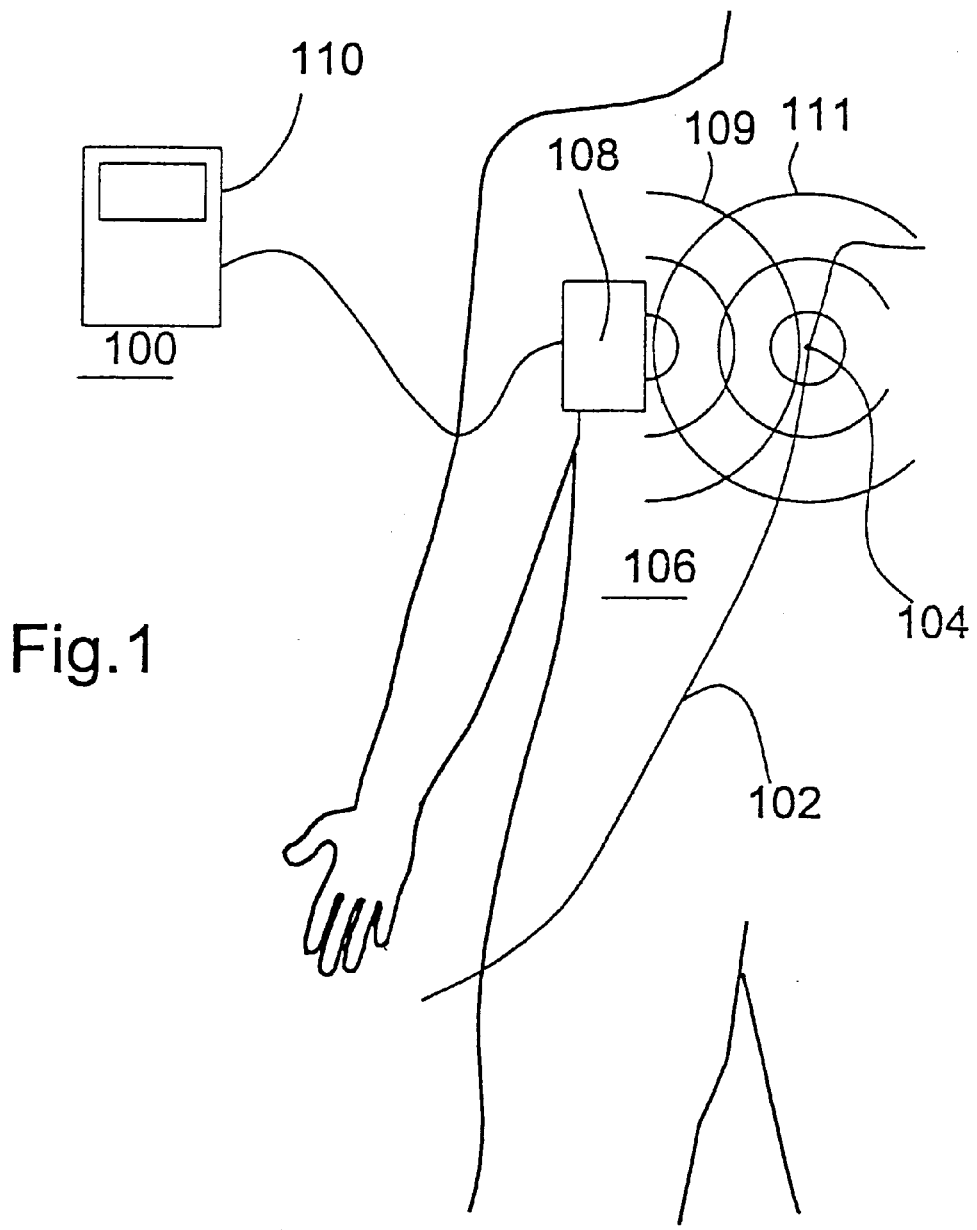
FIG. 1 is a schematic overview of a system according to the present invention.

In FIG. 1 a system according to the present invention, generally designated 100 is schematically illustrated.

It comprises a guide wire 102 provided with a resonance sensor 104 at its distal end portion. The resonance sensor may be of several types, and this will be discussed in further detail below. The guide wire and sensor is schematically shown to be inserted or implanted in the body of a patient 106. There is provided a transducer 108 for emitting excitation energy, said transducer being preferably located in the vicinity of the body, near the location where the sensor 104 is located, or even in contact with the body, and directed towards the sensor element 104, in such a manner that an emitted power (e.g. electromagnetic or ultrasonic) wave 109 hits the sensor element 104. The ultrasonic power incident on the sensor element is redistributed or modulated by the sensor element in such a way that the characteristics of the modulation corresponds to the variable or variables to be measured. The scattered ultrasonic wave 111 thus carries information about the measured, and conveys this information back to the transducer 108, which, when operating in the receiver mode brings a signal back to an electronic drive/control and detection unit 110, e.g. a PC, for signal analysis. Typically, the transducer 108 operates at a frequency of 0.1–10 MHz.

The transducer can be of various types depending on the type of sensor 104 being employed. Thus, if the sensor is of the electromagnetic type, i.e. being excitable by electromagnetic energy, the transducer may be of a type such disclosed in the articles mentioned in the discussion of the background of the invention.

Alternatively the sensor may be a mechanically resonating type sensor, in which case the transducer may be an ultrasonic transducer. An example of such a transducer is a piezoresistive plate made from a ceramic material, such as lead titanate-zirkonate. By applying voltage pulses to such a material, mechanical deformations will appear, which in turn will give rise to the emission of ultrasonic power. Conversely, such an element will also function as a receiver of ultrasonic waves. The transducers are state of the art and do not per se belong to the invention.

In a preferred embodiment the sensor is mounted on a guide wire. This means of inserting a sensor into a body is per se well known and does not form part of the invention. However, the provision of a resonance sensor of the type contemplated by the invention is novel and inventive, and brings about the possibility of wire less detection of physical variables, preferably physiological variables.

The present invention makes use of the transmission properties of human or animal tissue, to communicate power and information. In fact, power and information can be efficiently transmitted through human soft or hard tissue in a number of ways, including acoustic and electromagnetic waves. The invention makes efficient use of this property in redistributing or modulating the incident power of an acoustic or electromagnetic wave in such a way that information gathered by a sensor element can be accessible by external means. More specifically, the redistribution or modulation of power is performed by one or several resonating elements, exhibiting a degree of coupling towards the incident wave. The property of these resonators is to carry and transmit information linked to the physiological variables to be measured, i.e., pressure, flow or temperature, at the sensor location. By redistributing, or modulating the incident power, information about the variables to be measured is thus transferred to the surrounding medium and is thus externally accessible. In a preferred embodiment, the guidewire includes one wire without joints along its length. This is a preferred solution from a reliability point of view. Moreover, the guidewire includes sections of different bending flexibility, notably with maximum flexibility in the vicinity of the distal end, to prevent issue perforation.

The present invention has significant advantages compared to the previous known devices. First, it eliminates the need for a mechanical connection between the sensor and external equipment. Second, its use in permanently implanted devices also minimizes the risk of contamination and infection. Third, it has a simplified construction and improved mechanical properties. Four, it reduces the cost of manufacture of the sensor guide assembly. Five, it has the potential of improving overall system reliability by eliminating weak points.

Referring now to FIG. 2a, there will be seen a guidewire 202 having a distal end 224 and a proximal end 225. The guidewire preferably has a length of between 60 and 350 centimeters and an outer diameter of between 0.3 and 1.5 millimeters in order to be accommodated with the usual catheters. The guidewire 202, preferably, is constructed of a wire of a non-corrosive and bio-compatible material, such as stainless steel, titanium, memory metal such as NITINOL®, platinum, tungsten or the like.

The guidewire 202 also preferably has a maximum bending flexibility at or near its distal end 224, 226. To create the maximum bending flexibility at the distal end 224, 226 of the guidewire 202, the distal end 224, 226, preferably, is constructed such that it has a smaller cross-sectional area than the proximal end 225, as seen in FIGS. 2b and 2c, sections A—A and B—B respectively. The appropriate bending and torsional flexibility is essential to ensure proper mechanical operation of the guidewire 202 while inserting it through the body, for example, through bifurcated blood vessels. Preferably, the second having the highest bending flexibility extends, approximately, 20 to 30 millimeters from the tip of the guidewire 202. The guidewire 202 then gradually increases in thickness as shown in FIG. 1a.

As shown in FIG. 2a, a coil 206 can be wrapped around the distal end 224, 226 of the guidewire 202 to increase the guidewire's strength without substantially decreasing the bending flexibility of the guidewire 202.

The guidewire 202 has a slot 220 located about 30 to 50 millimeters from the tip of the guidewire. The slot 220, preferably, has a length of about 1 to 2 millimeters and a width of approximately 50 to 250 micrometers. The slot 220 contains the sensor element 210. The sensor element 210 is fixedly mounted in the slot 220, as seen in section B—B, for example, via an adhesive or without an adhesive.

In FIG. 3a a first preferred embodiment of the sensor and guide wire assembly 300 according to the invention is shown. It comprises a wire 302 of a non-corrosive and biocompatible material such as stainless steel, titanium, NITINOL®, platinum or tungsten, having a maximum bending flexibility in the vicinity of the distal end 304. As can be seen in the figure the wire 302 is of uniform thickness over the major part of its length from the proximal end towards the distal end, but about 30–35 cm from the distal it has been reduced in diameter in order to increase its flexibility. Preferably the diameter reduction is obtained by providing the major part of the reduction over a rather short distance, say 1–5 cm indicated at 312 in the figure, and than gradually further reducing the diameter along the next 30 cm or so, indicated at 314.

This section of the guide wire having the reduced diameter is enclosed in a coil 306, which is used in a preferred embodiment to maintain the same outer diameter over the entire length of the guide wire, while still retaining high bending flexibility. Also this coil will act as a kind of "roller bearing" inside a vessel, by virtue of the fact that the coil may rest against the inner walls of a vessel, while the core wire is rotatable. The coil 306 is attached by soldering or gluing, or possibly by threading it onto the wire. Alternatively it is contemplated to use a sleeve or tube of a polymer material enclosing a core wire made of memory metal.

After the 30 cm long section with reduced diameter and thereby increased flexibility, there is provided a thicker portion 316. The thickness is not abruptly increased but instead a tapered portion 317 is provided. This thicker portion forms the mounting site 318 for a resonance sensor 310. In this embodiment the mounting portion 316 has a diameter slightly smaller than that of the wire 302 at the proximal part, in order of that the coil 306 may enclose the mounting portion 316 partially over its length. The mounting portion 316 is provided with a slot 320 in which the sensor 302 is located and attached by suitable means such as gluing, bonding or soldering, or by any other appropriate means that meets the requirements to achieve the objects of the invention. The slot is preferably made by spark machining. The coil 306 will, as indicated above, cover only a part of the mounting portion 316, leaving an opening 322 through which the surrounding medium, e.g. blood or other body fluids, will access the sensor 302, which thereby will respond to changes in the environment.

The distal end 324 of the mounting portion 316 will again have a reduced diameter, such that very tip of the wire is about only 10–20% of the nominal diameter of the wire. The very tip is anchored in an end plug 326. The part extending from the point where the diameter of the mounting portion 316 begins to be reduced is enclosed in a coil 328, similar to the coil 326.

In FIG. 3b there is shown an alternative embodiment of the mounting site for the sensor 310. Here the slot 320 is recessed 326 further so as to form a "shelf" 328 on which the sensor 310 is mounted, whereby the sensor cantilevers out from said shelf 328 over the recessed part 326. This alternative is equally applicable to the embodiment of the sensor and guide wire assembly shown in FIG. 4, to be described below.

In FIG. 4a there is disclosed an alternative embodiment, which in the main is the same as the embodiment of FIG. 3a. Thus there is provided a wire 402 having increased bending flexibility near the distal end 404, achieved by a diameter reduction at 412 and than gradually over a distance. There is also provided a sensor mounting portion 416 having a recess 420 in which a sensor 410 is positioned. At the distal extension this embodiment is virtually identical to the embodiment of FIG. 3a.

However, there is one important difference, in that the mounting portion 416 is made thicker than in the embodiment of FIG. 3a. Thus, the diameter of the mounting portion 416 has substantially the same diameter as the nominal diameter of the wire 402. Therefore the coil 406 is not provided so as to cover the mounting portion, but will only be attached to it by gluing, soldering or threading at the tapered section 417.

In this embodiment the recess 420 can be made deeper, and if made sufficiently narrow it will offer adequate protection for the sensor without need for any protective cover.

In this embodiment it may be difficult to attach the coil 406 as shown in FIG. 4a. Thus, in FIG. 4b there is shown an alternative design where the core wire is made to a smaller diameter and thus the thicker portion 416 has a larger diameter. The coil is pulled over the core wire, and then the wire is inserted in a proximal tube 430. As shown, the wire 420 can extend only a small distance into the tube 430. However, it may equally well extend all the way up to the proximal end of the guide wire. This embodiment of the proximal portion is also applicable to the other embodiments of the assembly disclosed herein.

Figure 5A:
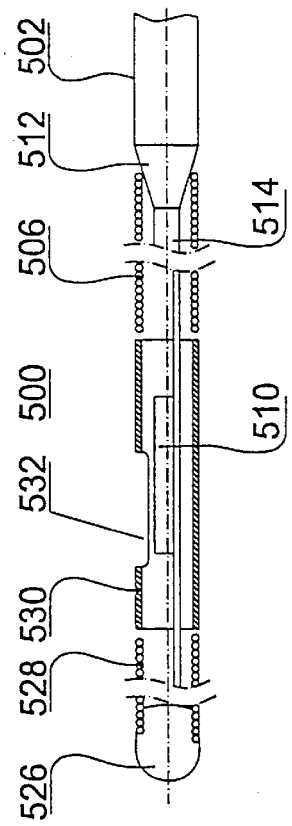
FIG. 5a is a longitudinal view of still another embodiment of a sensor and guide wire assembly according to the invention.

In FIG. 5a a still further embodiment of the sensor and guide wire assembly 500 is shown. It also comprises a wire 502 having a distal portion with higher flexibility. This is brought about by a first relatively short (1–5 cm) tapering portion 512, continuing in a thinner portion 514, gradually becoming thinner over a distance of about 35 cm, and finally anchored in an end plug 526. However, instead of providing a thicker mounting portion, as in the embodiments of FIGS. 3 and 4, a sensor 510 is simply mounted on the thin portion 514 of the wire 502, but at the same longitudinal position. The sensor 510 is protected by a protective tube 530, having a recess 532 through which the medium acting on the sensor 510 will have access.

Also in this embodiment there is provided a coil 506 covering the tapering part 512 and the thinner potion 515 for providing maximum strength while still retaining high bending flexibility. The coil is attached to the tube 530 at its ends by soldering, gluing or threading or any other suitable method. Thus the coil 506 does not cover the tube 530 but rather connects to its. Also on the distal side of the tube there is provided a coil 528.

In FIG. 5b, an alternative way of anchoring the wire in the distal end plug 526 is shown. It comprises a hook shaped structure 503 which is soldered to the tip 527 of the wire 502. This alternative anchoring principle is applicable to all embodiments disclosed herein.

Figure 6:
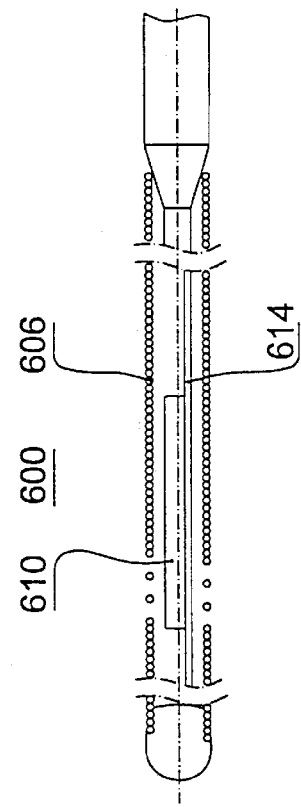
FIG. 6 is a longitudinal view of still another embodiment of a sensor and guide wire assembly according to the invention.

FIG. 6 illustrates a further embodiment, similar in design to the embodiment of FIG. 5, except that the sensor 610 is not protected by a tube. Instead a coil 606 is provided over the entire thinner portion 614 of the wire. The sensor 610 is mounted on the thin section 614 of the wire, and exposure to the surrounding medium is achieved by making the windings of the coil in a spaced apart configuration.

Figure 7:
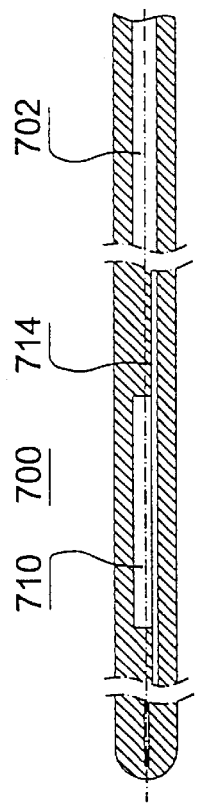
FIG. 7 is a longitudinal view of a still further embodiment of a sensor and guide wire assembly according to the invention.

In FIG. 7 there is shown an embodiment of a sensor and guide wire assembly wherein the sensor 710 is mounted on a thinner section 714 of the wire 702, and the entire assembly is embedded in polymer, which thus forms the external surface of the guide wire.

As indicated, it is to be understood the different variations of components or functions of the illustrated embodiments are interchangeable between the overall assemblies as illustrated in FIGS. 3–7.

Machining of wires and tubes to desired shapes and structures is preferably made by spark machining, although etching or possibly photolithographic techniques may be used.

It is to be understood that any type of resonance sensor according to the definition given previously herein may be employed, as long as the desired functionality is achieved.

One such prior art sensor that may be utilized in the system according to the present invention is disclosed in U.S. Pat. No. 5,808,210 and U.S. Pat. No. 5,747,705 (W. R. Herb et al.), the disclosures of which are incorporated herein in their entirety.

Below detailed descriptions of some examples of other possible sensors that may be used in the system and method of the invention will be given with reference to FIGS. 8a–e.

Figure 8A:
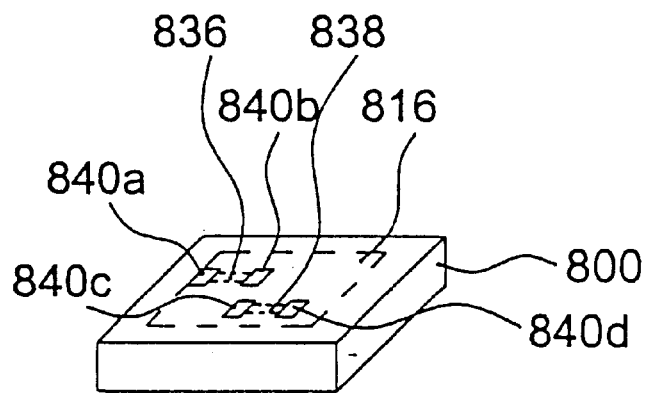
FIG. 8a–8e illustrate a first embodiment of the sensor element according to the invention.
Figure 8B:
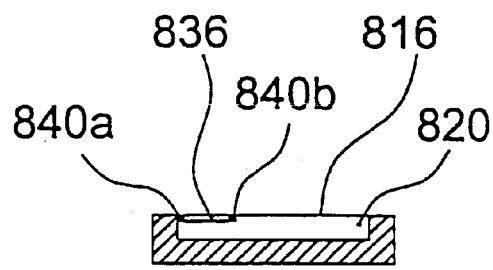
Figure 8C:
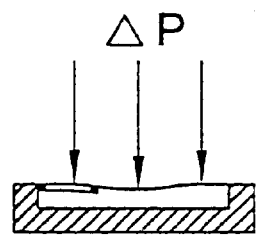
Figure 8D:
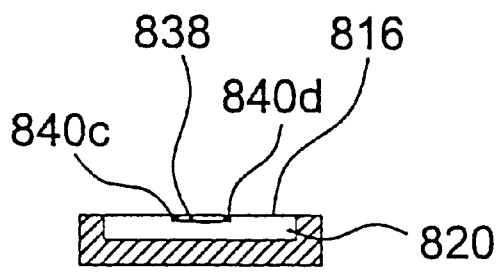
Figure 8E:
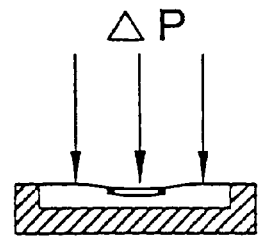

One preferred embodiment of a sensor element 800 according to the invention is shown in FIGS. 8a–8e. The sensor element 800 of FIGS. 8a–8e responds to pressure FIG. 8a corresponds to a perspective view of the sensor element 800. FIGS. 8b and 8c show a cross-section of the sensor element 800 including a cross-section of a beam element 836, without and with pressure being applied to the element, respectively. FIGS. 8d and 8e show another cross-section of the sensor element 800, including a cross-section of another beam element 838, without and with pressure being applied to the element, respectively.

Thus, The sensor element 800 is comprised preferably of a silicon die. The sensor element 800 should be designed and fabricated for the specific purpose of modulating or redistributing the incident power of an acoustic or electromagnetic wave. Moreover, the sensor element 800 should allow one of several variables, for example, temperature pressure or flow, to be accessed and determined using a device outside of the body, that is, located externally from the human or animal tissue. An advantageous simple acoustic modulator comprises a mechanical resonator using an elastic spring element combined with a mass element. The spring element preferably comprises a thin silicon diaphragm 816 that defines a cavity 820.

The top surface of the silicon die has a thin diaphragm 816 and two beam elements 836, 838. The beam elements 836, 838 are attached to the diaphragm by suspensions 840a–d at two points for each beam element 836, 838. The silicon substrate and the diaphragm enclose a cavity 820 to define a reference pressure for the pressure sensing element 800. The cavity 820 is preferably evacuated and hermetically sealed, allowing the sensor element 800 to measure absolute pressure.

The sensor element 800 preferably is 0.15×0.15×0.10 mm and is advantageously comprised, for the most part, of a silicon die, fabricated from a full wafer by batch processing. The die is constructed using techniques generally known as silicon surface micro-machining including, lithography, material deposition, etching, or the like.

The diaphragm 816 preferably has a thickness of 1 to 2 $\mu$m and lateral dimensions of 100×100 $\mu$m. The beam elements 836, 838, preferably, are thin, narrow polysilicon structures subjected to elongation strain, which can be controlled during deposition. The beam elements 836, 838 preferably are 0.5–1 $\mu$m thick, 1–3 $\mu$m wide, and 30–50 $\mu$m long.

As seen in FIGS. 8c and 8e, when pressure is applied, the elongation strains of beam elements 836, 838 will decrease and increase, respectively, due to the positions of the suspension 840a–840d and the characteristic bending movement of the diaphragm 816. The characteristic bending movement of the diaphragm 816 results from the pressure difference, $\Delta P$, over the diaphragm 816.

The beam elements 836, 838, define mechanical resonating elements. The resonance frequency of each beam element 836, 838 is determined by its elongation strain, which is analogous to a violin string. As seen in FIG. 8c, when pressure is applied, the tension of the beam element 836 decreases resulting in decreased resonance frequency. The opposite relationship results for beam element 838. The quality factor of the resonance frequencies may be very high, because the vibrations may operate in vacuum.

If the diaphragm 816 is subjected to periodic pressure variations from an incident ultrasonic wave, as described above, the diagram 20 will vibrate at the same frequency. If this frequency is very close to the resonance frequency of the beam element 836 or 838, then sustained oscillations of high amplitude will be induced in beam 836 or 838. If the incident ultrasonic power is then abruptly shut off, then the oscillations will persist and decay at a rate determined by the quality factor of the beam resonator. The beam resonator is also coupled to the diaphragm 816, which is connected to the surrounding tissue, thus, the beam oscillations will be radiated somewhat as ultrasound power. As a result, it is possible to detect the beam oscillations at a location that is remote from the sensor element 800.

Accordingly, the beam elements 836, 838 can be considered as temporary storage elements of acoustic power. When excited at a frequency close to the free oscillating frequency, or the resonance frequency, energy will be stored. The storage capacity is determined by the quality factor, and so is the rate of dissipation after the external ultrasonic source has been cut. In the sensor element of FIG. 8, the pressure information is coded as frequency, because the resonance frequency of beam elements 836, 838 is a function of pressure. The quality factor Q can also be used as the information carrier, rather than the frequency.

In another embodiment, the beam elements 836, 838 have different resonance frequencies. Different transducers having different operating frequencies, therefore, may be used to excite the beam elements 836, 838. One advantage of this arrangement is a resulting higher output signal level and sensitivity due to two measurements being taken rather than a single measurement. Another advantage is that, any common spurious factor will have a decreased effect on the efficacy of the system. One such spurious factor, in some instances, is temperature. Temperature can have a negative influence on the system, for example, when the device was calibrated at room temperature, but the measurements are being taken at body temperature. Accordingly, it is necessary to compensate for the temperature drift of the pressure sensing element 800. The compensation is easy when the sensor element 800 has two beam elements 836, 838 that have opposite sensitivity.

Another embodiment of the sensor element 800, includes a beam element that has a relatively constant elongation strain, even when the diaphragm 816 is bent. A beam element according to this arrangement is insensitive to pressure. The resonance frequency of such a beam element is a function of temperature resulting from a finite difference in a temperature coefficient of expansion between the materials used to construct the diaphragm and the beam elements. For example, the diaphragm may be made from single crystalline silicon and the beam may be made from polycrystalline silicon, which creates a temperature coefficient of expansion differential. It is possible, therefore, to use the sensor element 800 to measure pressure or temperature, or both, by simply designing the sensor element 800 in an appropriate manner. It is also possible to use the same sensor 800 to measure flow based on the principles of thermodilution.

Figure 9:
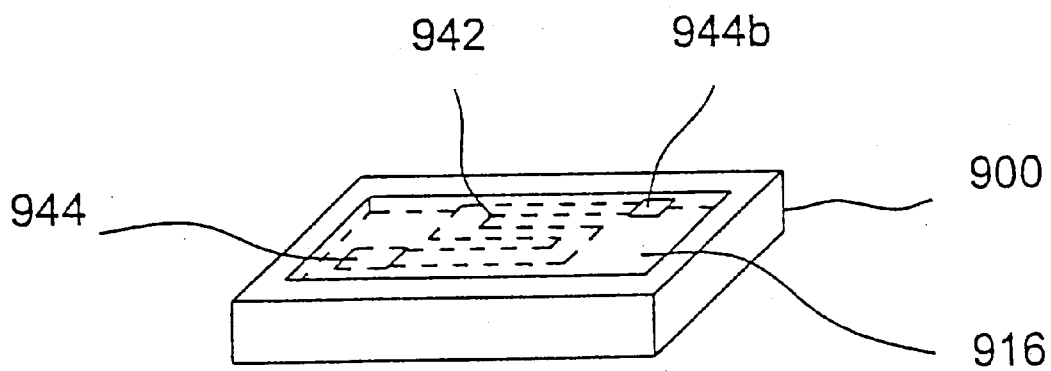
FIG. 9 illustrates an alternative embodiment of a sensor element according to the invention.

Another embodiment of the sensor element 800 invention is shown in FIG. 9. The sensor element 900 has a diaphragm 916 and a beam element 942 attached to the diaphragm 916 by suspensions 944a, 994b. The beam element 942 of FIG. 9 functions in a somewhat different manner as compared to beam elements 836, 838 of FIG. 8, in which the resonating frequency is a function of the elongation strain of the beam elements 836, 838. The beam element 942 of FIG. 9, on the other hand, has a rectangular cross section with a preferable width to thickness ratio of 5 or more. The beam element 942 is formed generally in an 'S'-shape, i.e., following a more or less curved line between the suspensions, thereby subjecting the beam element 942 to torsional strain when the diaphragm is subjected to external pressure. This property, in turn, results in a pressure dependence for resonant torsional vibrations. One advantage of the sensor element 800 of FIG. 0 over the sensor element 800 of FIG. 8 is that, to operate as a pressure dependent resonator, no internal strain is required. In all other respects, beam element 942 operates in the same manner as beam elements 836, 838.

Further sensor structures and manufacture thereof, usable for the purpose of this invention are disclosed in U.S. patent application Ser. No. 09/219,794, assigned to the same assignees as the present invention, and filed on the same day.

Figure 10A:
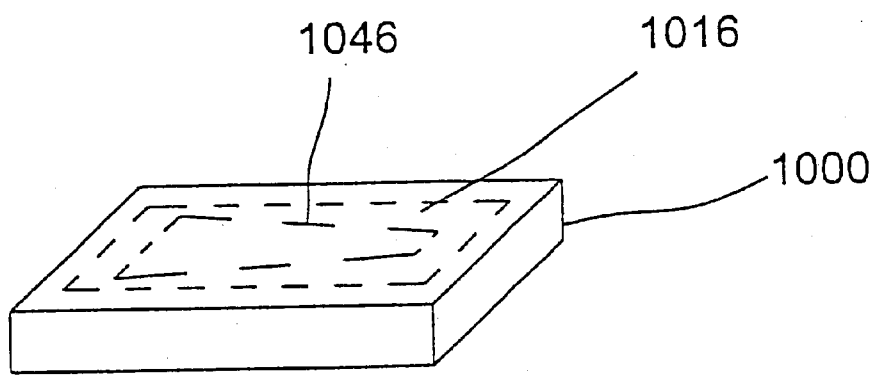
FIG. 10a illustrates another embodiment of a sensor element according to the invention.
Figure 10B:
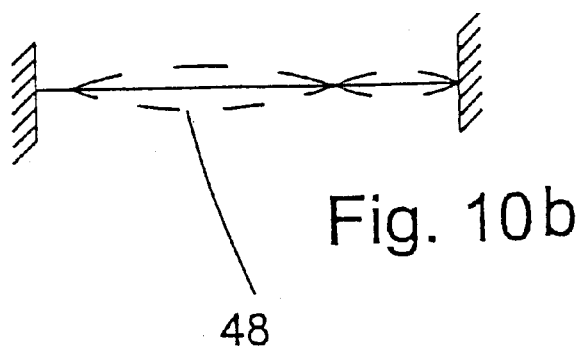

Yet another embodiment of the invention is shown in FIG. 10a. FIG. 10b shows a particular vibration mode 1048 of a stiffening element 1046. In FIG. 10a, the pressure sensor element 1000 has a diaphragm 1016 as in the embodiments of FIGS. 8 and 9. The diaphragm 1016 incorporates a stiffening element 1046 that preferably is comprised of an area with increased diaphragm thickness. In a preferred embodiment, the element 1046 has a trapezoidal shape to augment a particular vibration mode 1048 of the diaphragm, as shown in FIG. 10b, and to make this particular resonance frequency sensitive to pressure variations, which is analogous to the aforementioned dependencies with respect to FIGS. 8 and 9. The vibration mode 1048 corresponds to a second order resonance frequency that can also be excited by ultrasonic waves impinging on the diaphragm 1016. An advantage of the embodiment of FIG. 10a is that no separate beam elements are required to create a pressure dependent resonator.

Figure 11A:
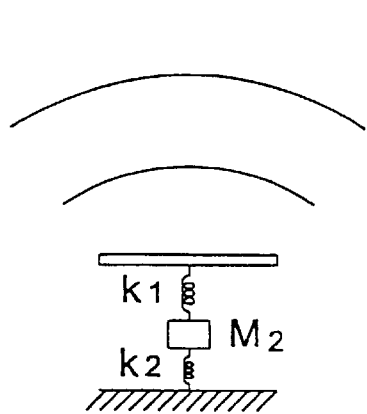
FIG. 11a is a schematic of the mechanical elements of an acoustically coupled resonating structure.

FIG. 11 shows two schematic drawings or circuit diagrams of resonator structures. A mechanical resonator network is shown in FIG. 11a and comprises two coupled resonators, having two mass-spring pairs, characterized by masses $M_1$, $M_2$ and spring constants $k_1$, $k_2$. Referring to FIG. 9, one of the resonators corresponds to beam element 942, and the other resonator corresponds to the diaphragm 916. The beam element 942 is characterized by its torsional spring constant and its moment of inertia for torsional motion. The diaphragm 916 is characterized by its mass and bending stiffness. According to the elementary theory of second order vibration systems, a mechanical resonator of mass M and spring constant k has a resonance frequency $f_{om}$ defined by $$f_{om} = \tfrac{1}{2}p^*(k/M)^{1/2} \tag{1}$$

Two weakly coupled resonators operating at different frequencies may be treated as mutually independent elements, which is one possible operational mode for sensor element 900 of FIG. 9. It is preferable to adjust the mass and stiffness of diaphragm 916 so that its resonant frequency is considerably higher than the resonance frequency of the beam 942. Thus, the mutual dependence of the resonances will be minimal. The diaphragm 916 operates within its flat frequency range, and the resonant oscillations solely depend on the pressure sensitive beam element 942. In some cases, however, it is advantageous to utilize the opposite condition, for example, to optimize power transfer to and from the resonator. For example, if the measured variable is coded as the quality factor Q of one of the resonators, it is advantageous to use two strongly coupled resonators operating at equal or nearly equal frequencies. Using the quality factor Q as the information carrying parameter is advantageous for temperature measurements, because the quality factor Q often strongly depends on temperature.

Figure 11B:
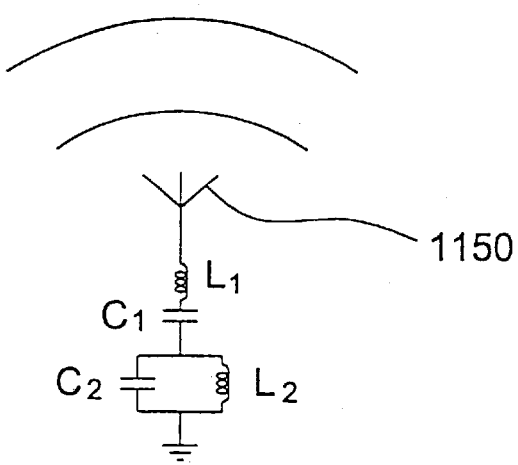
FIG. 11b is a schematic of an electromagnetically coupled resonating structure.

An embodiment of the sensor element 900, in which electromagnetic resonators are used, is shown in FIG. 11b. The electromagnetic resonators consist of an L-C network having two capacitors $C_1$, $C_2$ and two inductors $L_1$, $L_2$. This arrangement is wholly analogous to a mechanical resonator structure. The corresponding resonance frequency $f_{oe}$ for an L-C resonator is $$f_{oe} = \tfrac{1}{2}p^*(1/LC)^{1/2} \tag{2}$$

The capacitance C of a parallel plate capacitor is $$C = Aee_o/d \tag{3}$$

where A is the area of the plate, e, $e_o$ are the permittivity constants, and d is the distance between the plates. If one of the capacitor plates is a diaphragm of the kind shown in FIGS. 3 and 4, then its pressure-induced bending causes a variation of the capacitance, which, in turn, generates a change in the resonance frequency $f_{oe}$. Accordingly, a pressure sensor element having one or two L-C electromagnetic resonators responds to pressure analogously to the aforementioned mechanical resonator.

In the electromagnetic embodiment shown in FIG. 11b, the two L-C resonators are mutually coupled, which is analogous to the resonators $M_1k_1$ and $M_2k_2$ of FIG. 6a. Furthermore, a certain coupling to the ambient medium is necessary to ensure that incident electromagnetic waves induce oscillations in the L-C resonator, which carry information about the physiological variable to be measured. Likewise, a certain coupling is necessary to enable detection, via external means, of the free, sustained oscillations of the resonator after the incident electromagnetic wave has been cut. In FIG. 11b, an antenna 1150 couples the L-C network and the ambient medium.

In both the mechanical and the electromagnetic arrangements, at least one of the resonators must have a high quality factor Q. Otherwise, it may not be possible to detect the free oscillations, because of interference from scattering and reflecting of the primary incident wave. In practice, it is preferable that the quality factor Q be greater than 10. In high performance systems, the quality factor is preferably about 100. Higher Q factors are more easily realized in mechanical resonators operating in vacuum than in electromagnetic ones. Acoustic and mechanical implementations of the system are, therefore, preferred in applications that require high performance systems.

Figure 12A:
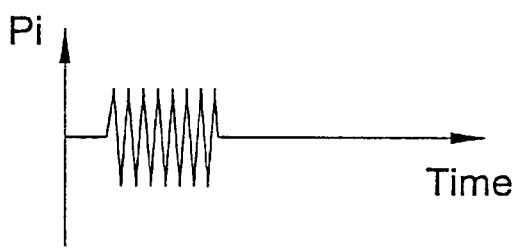
FIGS. 12a–12b depict a graphical representation of incident and redistributed or modulated power according to one embodiment of the invention.
Figure 12B:
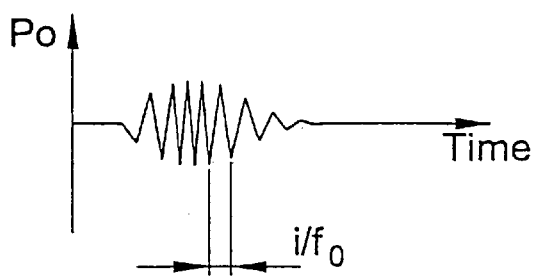

Typical waveforms for excitation and detection are shown in FIGS. 12a and 12b, respectively. The excitation waveform is a burst of sine waves. In an acoustic/mechanical system, a preferable excitation frequency is 1 MHz, and the burst consists of 10–1000 periods, depending on the quality factor Q of the resonator. A larger number of periods is more desired when the quality factor Q is high, because a larger oscillation amplitude is induced. FIG. 12b depicts such a built-up of the oscillations. When the external power source causing excitation is switched off, power will be emitted from the resonator and decays at a rate also determined by the quality factor Q. The frequency of the free oscillations $f_o$ is equal to the resonance frequency of the resonator. These oscillations are detectable externally, because power is partially radiated as a result of the coupling between the resonator and the ambient medium.

The burst of sine waves according to FIG. 12 is followed by a relaxation period until the next burst. The relaxation periods are preferably longer than the duration of the bursts.

Figure 13:
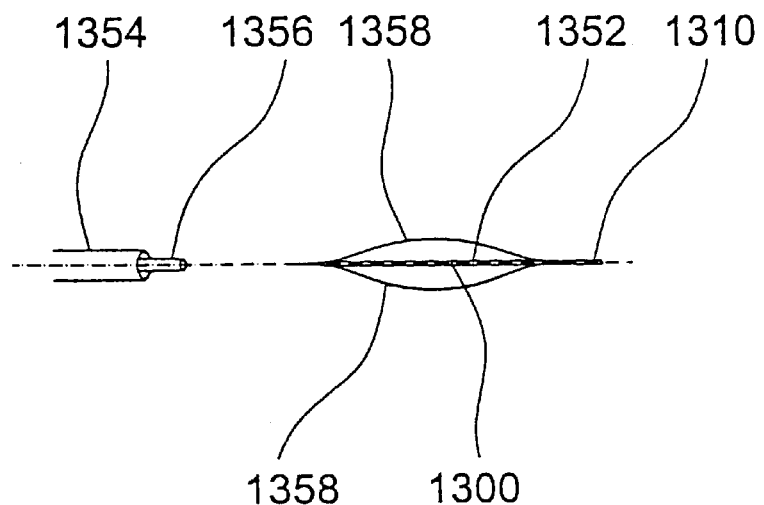
FIG. 13 is a side view of an embodiment of the sensor according to the invention adapted for permanent or temporary implantation within a human or animal body.

Another embodiment of the sensor and guide wire assembly is shown in FIG. 13. This embodiment is preferable in situations where the sensor element 1300 is permanently or temporarily implanted in the patient's body. The sensor element 1300 may be placed in the patient on a long-term basis, for example, to monitor intracranial, intrauterine, or intraurinary pressure. For long-term applications, the sensor element 1300 is permanently attached to a tubular element 1352 that temporarily encloses the guidewire 1310. The embodiment also includes a catheter 1354 having a relatively large inner diameter, to enclose both a thinner catheter 1356 and the tubular element 1352, which includes the sensor element 1300, the guidewire 1310, and fixing spring elements 1358. The fixing spring elements 1358 are permanently attached to the tubular element 1352. The thinner catheter 1356 also encloses the guidewire 1310, but its inner diameter, preferably, is not sufficient to enclose the tubular element 1352. When the guidewire 1310 is withdrawn (to the left in FIG. 13), the tubular element containing the sensor 1300 is detached and left in place. The fixing elements 1358, preferably comprising spring wires will keep the tubular element 1352 in a fixed radial position against, for example, the walls of a body fluidic chamber, such as an intracranial cavity, the uterine, or the urinary bladder.

Figure 14:
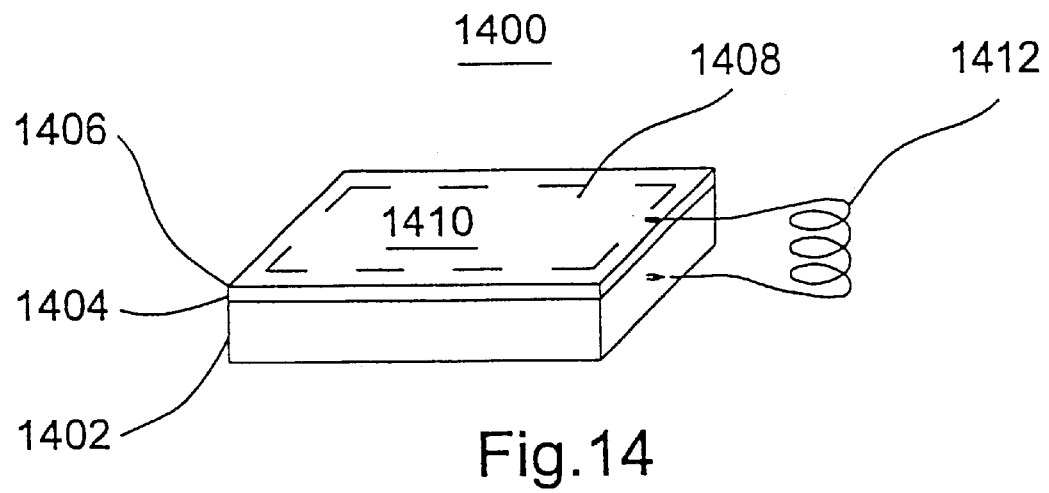
FIG. 14 shows an embodiment of the sensor element based on electromagnetic resonance.

In FIG. 14 there is shown an embodiment of a sensor exhibiting electromagnetic resonance. It comprises a silicon substrate 1402 on which there has been provided an insulating first layer 1404 of silicon dioxide. On top thereof is a second layer 1406 of e.g. silicon, that may be applied by direct bonding. In the second layer there has been formed a cavity 1410 such that a thin diaphragm 1408 is formed covering the cavity, which is evacuated. This diaphragm 1408 and the substrate 1402 form members of a parallel plate capacitor. When the diaphragm is subjected to pressure, it is deflected, thus causing a change in capacitance of the capacitor. To complete the L-C circuit an inductor 1412 is connected across the plates, i.e. the substrate 1402 and the diaphragm 1408.

Additional advantages and modifications will readily occur to those skilled in the art. Therefore, the invention in its broader aspects is not limited to the specific details, and representative devices, shown and described herein. Accordingly, various modifications may be made without departing from the spirit or scope of the general inventive concept as defined by the appended claims and their equivalents.

What is claimed is:

1. A method for measuring a physiological variable, comprising the steps of:
    (a) inserting a guidewire into a patient's body;
    (b) transmitting waves to a sensor mounted on said guidewire;
    (c) causing said sensor to resonate by said waves, said resonance being a function of a physiological variable; and
    (d) receiving resonance waves representing a measurement of the physiological variable.

2. A method for measuring a physiological variable as claimed in claim 2, further comprising the step of analyzing said resonance waves.

3. A method for measuring a physiological variable as claimed in claim 1, wherein said waves are transmitted through the body to the sensor, and said waves are redistributed by the sensor and received external to the body.

4. A method for measuring a physiological variable as claimed in claim 1, further comprising the step of (e) ceasing transmitting waves.

5. A method for measuring a physiological variable as claimed in claim 4, wherein step (a) through (e) are repeated at least once.

6. A method for measuring a physiological variable as claimed in claim 4, wherein said ceasing step is longer in duration than said transmitting step.

* * * * *